US00PP11862P2

(12) United States Plant Patent
Roberson

(10) Patent No.: US PP11,862 P2
(45) Date of Patent: May 8, 2001

(54) HEMEROCALLIS HYBRID PLANT NAMED 'ROBBOBELI'

(76) Inventor: Robert J. Roberson, 31706 E. Pink Hill Rd., Grain Valley, Jackson County, MO (US) 64029

( * ) Notice: Subject to any disclaimer, the term of this patent is extended or adjusted under 35 U.S.C. 154(b) by 0 days.

(21) Appl. No.: 09/249,101

(22) Filed: Feb. 12, 1999

(51) Int. Cl.[7] ..... A01H 5/00
(52) U.S. Cl. ..... Plt./312
(58) Field of Search ..... Plt./312

*Primary Examiner*—Bruce R. Campell
*Assistant Examiner*—Anne Marie Grünberg
(74) *Attorney, Agent, or Firm*—Rothwell, Figg, Ernst & Manbeck

(57) ABSTRACT

The new and distinct daylily plant as substantially shown and described, particularly characterized by its ability to adapt, grow and perform well in a wide range of USDA zones, it's compact growth habit, it's unique near-white blooms, it's above average increase (bunch formation) rate in it's color class, and it's tendency to rebloom late in the season.

2 Drawing Sheets

SUMMARY OF THE INVENTION

This invention relates to a new and distinct daylily distinguished by it's "near white" (so pale that it is visually "white" to the eye) colored blooms with diamond dusting, it's tendency to rebloom late in the season, it's ability to adapt and perform in a wide range of USDA zones, it's above average increase rate (bunch formation) in it's color class, and it's compact growth habit.

BACKGROUND OF THE INVENTION

This new variety of daylily plant originated as a seedling selected from a group of seedlings planted by me at my ranch in Grain Valley, Mo., and resulted from my crossing of the clonal cultivar 'Joan Senior' (not patented) with the variety 'Sea Gull' (not patented). My objective was to produce a plant having white blooms and compact growth habit. A further objective was to produce such a plant that would be both cold hardy, heat tolerant, have above-average bunch formation rate and repeat blooming.

This new plant was selected for propagation because it most closely possessed the advantageous features that I sought and asexual reproduction of the selected plant was accomplished by division at the crown or basal plate which is the area where the roots and foliage meet.

During the course of propagation of this new plant at my daylily ranch in Grain Valley, Mo., I have observed that the new plant has the tendency to rebloom late in the season, has unique "near white" blooms which abciss approximately 30% quicker than the average of other daylilies of this color category, and has consistently compact growth habit. Furthermore this plant has an above-average increase or bunch formation rate (7 fans compared to 4 fans for the average near-white daylily) in its color class, and is cold hardy and particularly capable of adapting, growing and performing well across five USDA zones (4–8) according to test data from the All American Daylily Selection Council (AADSC). The inventor has determined that the traits described and illustrated herein are stable and firmly fixed. I have chosen to identify this new cultivar as Hemerocallis 'Robbobeli'. This cultivar is being marketed in the United States under the name LADY ELIZABETH™.

BRIEF DESCRIPTION OF THE DRAWING

The accompanying photograph shows the new and distinct cultivar as nearly true as is reasonably possible to make the same, in a color illustration of this character.

DETAILED DESCRIPTION

Figure 1:
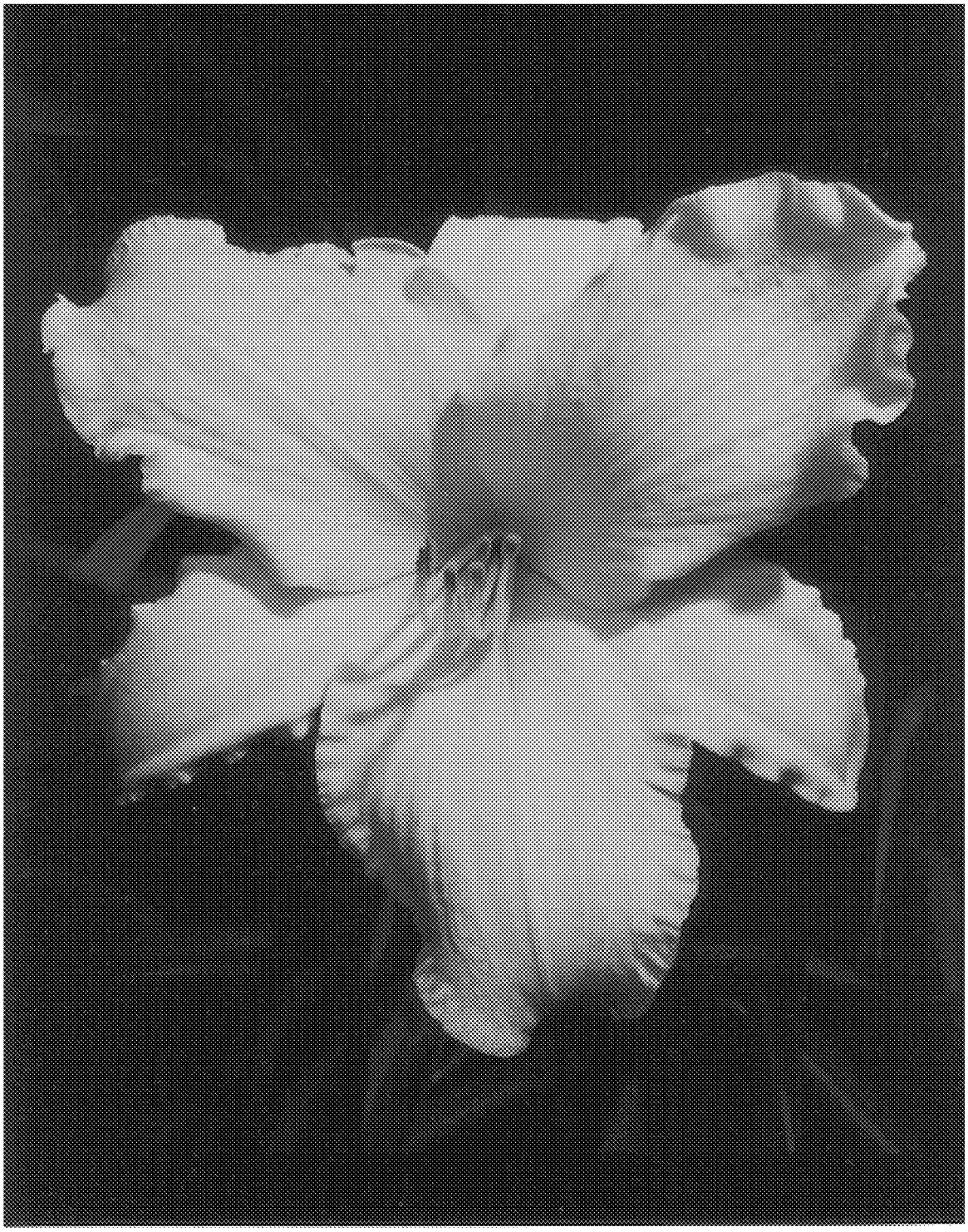
FIG. 1 illustrates the face view of the flower.
Figure 2:
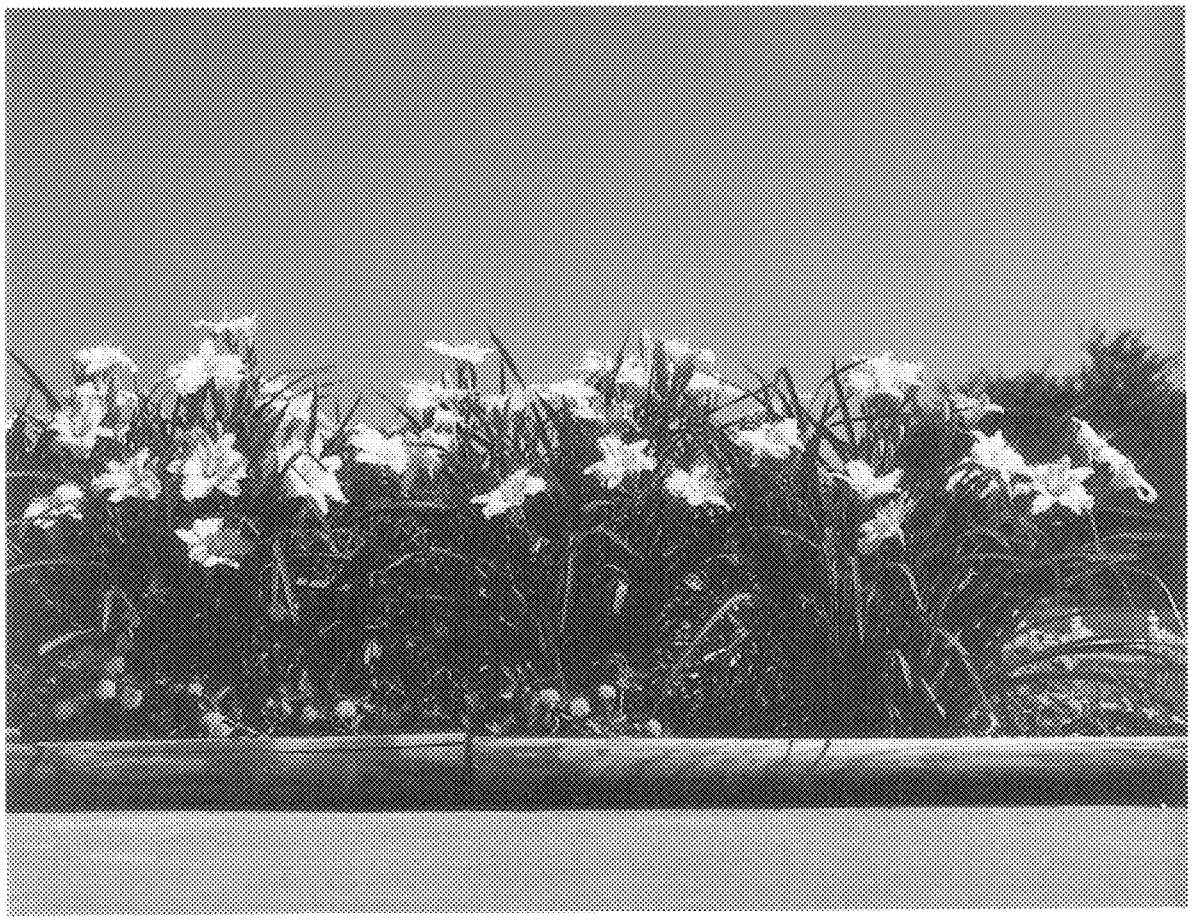
FIG. 2 illustrates the whole plant.

The following is a detailed description of my hybrid daylily cultivar based upon observation of plants grown at Grain Valley, Mo. during May, 1993 through October, 1997. All colors being noted as compared with the Pantone Matching System (PMS), except the dominate bloom color (near white) being noted as compared with The Royal Horticulture Society Colour Chart (R.H.S.). The measurements and colors were recorded from mature plants grown in the vicinity of Grain Valley, Mo. and from trial sites for the All American Daylily Selection Council.

THE PLANT

Origin: It should be noted that the plant was initially selected from a daylily planting being grown near Grain Valley, Mo. in a cultivated area and has since been a sexually reproduced by root division (division at the crown or basal plate which is the area where the roots and foliage meet) in the vicinity of Grain Valley, Mo. with the new and distinct characteristics stated herein, found to be maintained through successive generations as before recited.

Parentage:

*Seed parent.*—Hemerocallis Hybrid 'Joan Senior' (not patented.

*Pollen parent.*—Hemerocallis Hybrid 'Seagull' (not patented).

Classification:

*Botanic.*—Hemerocallis hybrid.

*Commercial.*—Daylily cultivar 'Robbobeli'.

Form: Single stem, erect and stately scape from a fan shaped plant made up of narrow arching grass-like, long keeled glabrous leaves 2-ranked at the base of the scape.

Foliage:

*Quantity.*—Abundant, a mature plant having about 12 leaves

*Leaf size.*—About 1.1" wide and about 19.7" average in length.

*Leaf shape.*—Linear and long keeled with entire margins.

*Texture.*—Glabrous.

*Color.*—Immature leaf, top and under side — Green PMS #370; Mature leaf, top side —Green PMS #364; underside —Green PMS #363.

*Clump foliage height (*24 month maturity).—16" average in height; 26.6"average in width.

*Plant bunch formation rate.*—An average increase of 7 plants per 24 month period compared to an average of 4 plants for the same period for the average plant in this color class. This increase or bunch formation data was collected by the AADSC. The clumps should be divided or separated every 3–5 years depending on the USDA zone and the increase rate. This separation is to maintain optimum growth and bloom beauty. The specimens will continue to flower for many years without division although the quality of performance will be diminished.

Scape:

*Color.*—Green (PMS #364).

*Height.*—About 17.3".

THE BUD

Form: Modified (Slightly wider at the mid-point) oblanceolate.

Size (day before opening):

*Length.*—About 5 cm.

*Width.*—About 2 cm.

Opening rate: About 11 hours.

Length bloom is open: About 16 hours, i.e., an "extended" bloomer per American Hemerocallis Society terminology.

Color: When sepals first divide — pale lime green (PMS #372).

Peduncle:

*Character.*—Rigid and sturdy.

*Color.*—Green (PMS #364).

THE FLOWER

Blooming habit: Flowers begin to appear on the established plant in mid-season (or the middle of the hemerocallis blooming season which is referred to as "peak bloom") and then repeat bloom with 1–2 more cycles of scape production, depending on USDA zone. 'Robbobeli' blooms for an average period of 44 days (compared to the average daylily tested by the AADSC, which has an average bloom period of 21 days).

Flower size:

*Diameter.*—About 5¼".

*Depth.*—About 2".

Shape: Triangular and recurred

Borne: Singly on the branchlets of a sturdy, erect rachis which is ramulus; each scape has at least four or five peduncles which divides into twelve or fifteen pedicles.

Number of blooms per scape: 10–13 average.

Petalage: The flower consists of six perianth segiments (tepals) consisting of three sepals (the outer segments) and three petals (the inner segments) all in an imbricated arrangement.

THE SEPALS

Shape: Oblanceolate with slightly undulated entire margins and an acuminatre apex.

Size: About 3" long and 1.5" wide.

Texture: Ribbed, lightly creped, and diamond dusted.

Color: Near-white (RHS 155D) with yellow-green throat (PMS 393) and green heart (PMS 377).

THE PETALS

Shape: Broadly obovate with entire undulated margins and a broadly cuspidate apex.

Color: Near white (RHS 155D) with yellow-green throat (PMS 393) and green (PMS 377) heart.

Texture: Ribbed, lightly creped, and diamond dusted.

Size: About 2.3" wide; 3" long.

Effect of weather: Resistant to sun andrain; petal turgidity holds well.

Fragrance: Slightly sweet floral scent

Disease resistance: This cultivar, as most hemerocallis, has not been noted to be very susceptible to plant disease Lasting quality: Good lasting quality due to flower segments (tepals) having thick, moderately spongy consistency which aids in fresh and turgid blooms throughout the day. As is typical for hemerocallis, blooms are only open for one day.

THE REPRODUCTIVE ORGANS

Stamens:

*Number.*—Six to eight.

*Arrangement.*—Inserted individually at the summit of the perianth tube.

*Anthers.*—Arrangement: Introrose; Size: 5 mm; Color: Brown (PMS #438).

*Filaments.*—Slender and 4 cm in length; Color: White (RHS #155D).

*Pollen.*—Yellow (PMS #109).

Pistils

*Number.*—One.

*Style.*—Length — 7 cm; Color — White (RHS #155D).

*Stigma.*—Color: White & glistening.

*Character of ovaries.*—Three celled.

*Shape.*—Oblong, becoming a loculicidal 3-valved capsule.

THE FRUIT (SEED POD)

Shape: The seed pod is an ovoid capsule

Color: Ranges from pale green (PMS #372) to olive brown (PMS #140) at maturity.

Fertility: Yes, this cultivar is fertile both ways, i.e., the pollen is fertile for application to the pistil of another cultivar and the pistil of this cultivar can receive pollen from another cultivar.

Size (at maturity): About ⅞" wide by 1" in length.

GENERAL OBSERVATIONS

'Robbobeli', with it's near-white, diamond dusted blooms, it's compact growth habit, it's tendency to repeat bloom late in the season, it's ability to adapt and perform in a wide range of USDA zones, it's dormant foliage, it's light fragrance, and it's above average bunch formation rate is an improved hemerocallis cultivar in the white color category.

COMPARISON TO KNOWN VARIETIES

'Robbobeli' may be compared with known varieties along the following lines:

As compared to the seed parent, 'Joan Senior', 'Robbobeli' is a distinct cultivar because of it's lighter color of bloom and it's improved cold hardiness over 'Joan Senior', it's faster bunch formation rate (7 fans in 24 months compared to 5 fans for 'Joan Senior' in the same period), it's more compact growth habit (17.3" scape height compared to 25" scape height for 'Joan Senior' and it's improved bloom abscission, i.e., drops it's spent blooms more quickly than 'Joan Senior' giving a "cleaner" appearance in the landscape.

As compared to the pollen parent 'Seagull', 'Robbobeli' is an improved cultivar because it is more compact than 'Seagull' (17.3" in height compared to 26" in height), it is more cold hardy than 'Seagull', has a fuller bloom form than 'Seagull' ('Robbobeli' petals are 2.3" in width compared to 'Seagull' petals of 1.7"in width), and has more bloom turgidity which gives superior lasting quality of the bloom.

I claim:

1. The new and distinct daylily plant as shown and described herein.

* * * * *